(12) United States Patent
Ueda et al.

(10) Patent No.: US 8,353,399 B2
(45) Date of Patent: Jan. 15, 2013

(54) PREPARATION-AT-USE DEVICE COMPRISING PRE-FORMED HYDROGEL PRODUCT

(75) Inventors: Akihiro Ueda, Kobe (JP); Koishiro Masuda, Osaka (JP); Kimio Tamiya, Kashihara (JP); Haruhiko Kajimoto, Higashisumiyoshi-ku (JP); Masahiko Ishimoto, Kanonji (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/282,568

(22) Filed: Oct. 27, 2011

(65) Prior Publication Data

US 2012/0041396 A1 Feb. 16, 2012

Related U.S. Application Data

(62) Division of application No. 12/944,047, filed on Nov. 11, 2010, now Pat. No. 8,066,117, which is a division of application No. 10/864,564, filed on Jun. 9, 2004, now Pat. No. 7,854,938.

(60) Provisional application No. 60/477,546, filed on Jun. 11, 2003.

(51) Int. Cl.
*B65D 25/08* (2006.01)
*A61K 2/00* (2006.01)

(52) U.S. Cl. .......................... 206/221; 206/219; 424/400

(58) Field of Classification Search .................. 206/219, 206/221; 424/400
See application file for complete search history.

(56) References Cited

U.S. PATENT DOCUMENTS

| | | | |
|---|---|---|---|
| 4,927,408 A | 5/1990 | Haak |
| 5,084,008 A | 1/1992 | Phipps |
| 5,393,305 A | 2/1995 | Cohen |
| 5,935,593 A | 8/1999 | Ron |
| 5,984,953 A | 11/1999 | Sabin |
| 6,010,706 A | 1/2000 | Candau |
| 6,138,312 A | 10/2000 | Cummings |
| 6,322,798 B1 | 11/2001 | Candau |
| 6,510,561 B1 | 1/2003 | Hammond et al. |
| 2001/0007671 A1 | 7/2001 | Gueret |
| 2003/0113356 A1 | 6/2003 | Deckner |
| 2003/0124162 A1 | 7/2003 | Ueda et al. |

FOREIGN PATENT DOCUMENTS

| | | |
|---|---|---|
| CA | 2306283 | 2/2000 |
| EP | 0904779 A | 3/1999 |
| JP | 6336413 A | 12/1994 |
| JP | 2000297008 | 10/2000 |
| WO | WO0009414 A1 | 2/2000 |
| WO | WO0178678 A1 | 10/2001 |

*Primary Examiner* — Paul V. Ward
(74) *Attorney, Agent, or Firm* — S. Robert Chuey

(57) ABSTRACT

Disclosed is a preparation-at-use device comprising: (1) a pre-formed hydrogel component packaged in a first compartment; the pre-formed hydrogel component comprising a gelling agent and a solvent; and (2) a benefit component packaged in a second compartment; the benefit component comprising at least one compound that is unstable when contacted with the pre-formed hydrogel component; wherein the first and second compartments are separately packaged prior to use, and wherein the device comprises means for contacting the pre-formed hydrogel component and benefit component upon use.

6 Claims, 3 Drawing Sheets

PREPARATION-AT-USE DEVICE COMPRISING PRE-FORMED HYDROGEL PRODUCT

CROSS REFERENCE TO RELATED APPLICATION

This application is a divisional of U.S. application Ser. No. 12/944,047 filed on Nov. 11, 2010, now U.S. Pat. No. 8,066,117 which is a divisional of U.S. application Ser. No. 10/864,564 (now U.S. Pat. No. 7,854,938), filed on Jun. 9, 2004, which claims the benefit of U.S. Provisional Application No. 60/477,546, filed on Jun. 11, 2003.

BACKGROUND

Pre-formed hydrogels made of gelling agents provide unique benefits to various consumer products due to its formed, yet flexible physical characteristics. Pre-formed hydrogel patch and mask devices are useful for cosmetic and dermatological treatment products such as for delivering skin care actives, percutaneously deliverable pharmaceuticals, and for promoting healing of burns or wounds. Edible pre-formed hydrogel sheets and objects provide nutritional products and snacks having distinctive appearance, taste, and oral texture; and oral administrative pharmaceuticals.

Particularly in the skin treatment area, the use of specialty cosmetics such as packs and masks are increasing in popularity in that they are effective, relatively safe, and reasonably priced compared to other treatments such as chemical peeling, laser surgery, photofacial, and others. PCT publication WO 01/78678 and co-pending U.S. application 60/339,287 relate to a pre-formed hydrogel product for effectively delivering skin benefit agents to the skin, hair or nails, the device comprising a skin benefit agent in the form of a coating composition for the pre-formed hydrogel.

While these pre-formed hydrogel products are suitable for delivering a variety of skin benefit agents to the skin, there are certain skin benefit agents and other chemical compounds that cannot be formulated with the product, as being unstable with the pre-formed hydrogel. For example, certain compounds react with the pre-formed hydrogel and enhance synerisis, enhance stiffening, or produce unaesthetic color and/or odor. All of these results may significantly affect product performance and/or aesthetics. Such factors limit the scope of compounds that can be formulated with the pre-formed hydrogel products.

Based on the foregoing, there is a need for a pre-formed hydrogel product that can be formulated with a wide variety of compounds, and can be suitably used by the consumer. Further, there is a need for such a product that can be provided at low cost.

None of the existing art provides all of the advantages and benefits of the present invention.

SUMMARY

The present invention is directed to a preparation-at-use device comprising:
(1) a pre-formed hydrogel component packaged in a first compartment; the pre-formed hydrogel component comprising a gelling agent and a solvent; and
(2) a benefit component packaged in a second compartment; the benefit component comprising at least one compound that is unstable when contacted with the pre-formed hydrogel component;

wherein the first and second compartments are separately packaged prior to use, and wherein the package comprises means for contacting the pre-formed hydrogel component and benefit component at-use.

The present invention is further directed to a device wherein the pre-formed hydrogel component has a first surface having a specified texture, and the benefit component has a specified viscosity.

These and other features, aspects, and advantages of the present invention will become better understood from a reading of the following description, and appended claims.

BRIEF DESCRIPTION OF THE FIGURES

While the specification concludes with claims particularly pointing out and distinctly claiming the invention, it is believed that the present invention will be better understood from the following description of preferred, nonlimiting embodiments and representations taken in conjunction with the accompanying drawings in which:

DEFINITIONS

Figure 1:
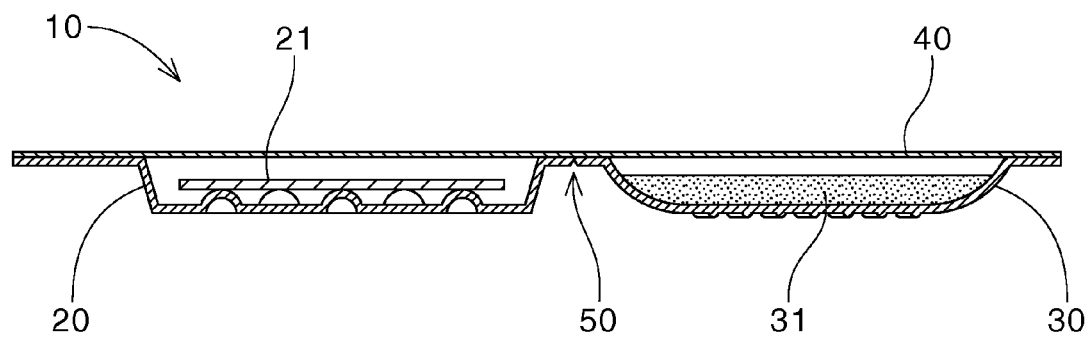
FIG. 1 is a sectional view of a preferred embodiment of the device of the present invention with the thickness of a packaging material being inflated.

All cited references are incorporated herein by reference in their entireties. Citation of any reference is not an admission regarding any determination as to its availability as prior art to the claimed invention.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials. All measurements are conducted at 25° C. unless otherwise specified.

All ingredients such as actives and other ingredients useful herein may be categorized or described by their cosmetic and/or therapeutic benefit or their postulated mode of action. However, it is to be understood that the active and other ingredients useful herein can, in some instances, provide more than one cosmetic and/or therapeutic benefit or operate via more than one mode of action. Therefore, classifications herein are made for the sake of convenience and are not intended to limit an ingredient to the particularly stated application or applications listed.

The term "pre-formed" as used herein, means that the object is manufactured into a form having a predetermined shape and size, wherein the object may be removed from any associated packaging and placed or draped onto the target surface by the fingers without further preparative steps by the user. The term "pre-formed" also means that, when manufacturing is completed, the object substantially retains its shape at the desired normal storage temperature when lying on a flat surface. The composition may nevertheless flex or be deformed when applied to an uneven surface or if impressed.

The term "free of supporting substrate" as used herein, means the pre-formed hydrogel is uniform and unilamellar in composition, with no additional substrate or layer for aiding in the structure or integrity of the pre-formed hydrogel.

DETAILED DESCRIPTION

While the specification concludes with claims particularly pointing out and distinctly claiming the invention, it is believed that the present invention will be better understood from the following description.

Preparation-at-Use Device

The present invention relates to a device that is specifically designed to prepare final products at-use, typically within about 60 minutes, preferably within about 10 minutes prior to use, suitably referred to as products for "preparation-at-use". Preparation-at-use devices are known in the art, and comprise at least 2 separate compartments comprising interim components which are contacted with each other upon use. A preparation-at-use device is designed so that the interim components are not contacted with each other during storage. Further, the packaging for a preparation-at-use device is preferably designed so that the preparation of the final product, such as mixing of the interim products, can be done by utilizing one of the compartments of the package.

The present invention relates to such preparation-at-use device which is suitable for delivering to the user at least two interim components, the interim components being at least a pre-formed hydrogel component and a benefit component, the benefit component being unstable when contacted with the preformed hydrogel component. Referring to FIG. 1, the present device (10) comprises at least two compartments for separately packaging the interm component, namely the pre-formed hydrogel component (21) in a first compartment (20) and the benefit component (31) in a second compartment (30). The pre-formed hydrogel components herein are typically relatively vulnerable to change of humidity, particularly excessive or rapid drying. Drying beyond a certain extent, depending on the composition, will decompose or deform the pre-formed hydrogel by destroying its gel structure. Therefore, the packaging for the present device is made of materials which have low water vapor permeability to minimize drying out of the interim components. The first and second compartments may be made of a same sheet of relatively rigid plastic material having concaved openings which are sufficiently distant from each other, and are sealed with a common releasable liner (40) which is made of, for example, a plastic, aluminum, or laminate film.

Figure 2:
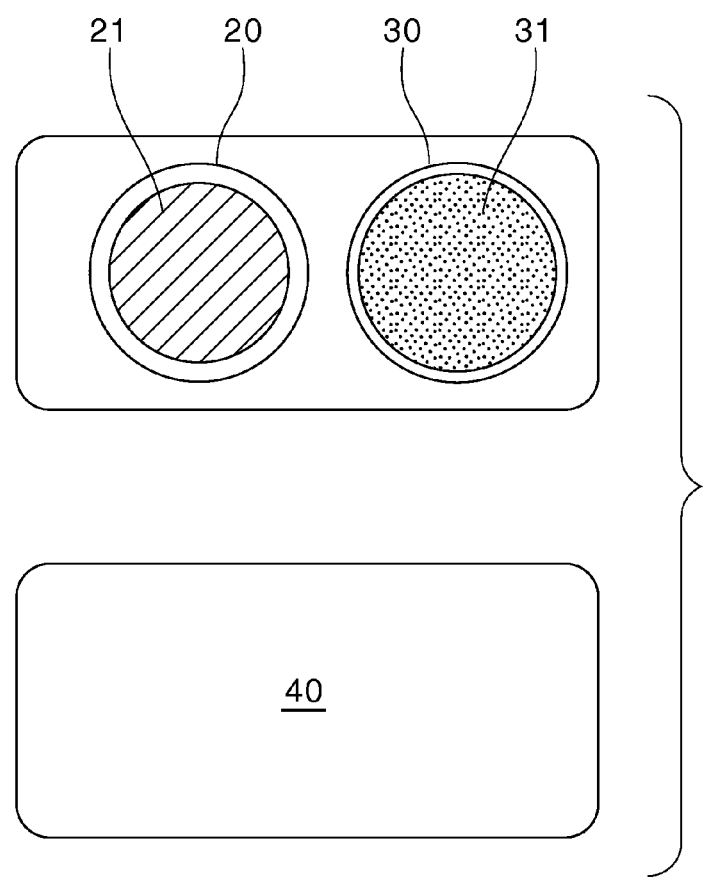
FIG. 2 is a perspective view of a preferred embodiment of the device of the present invention with a seal liner freshly removed.
Figure 4:
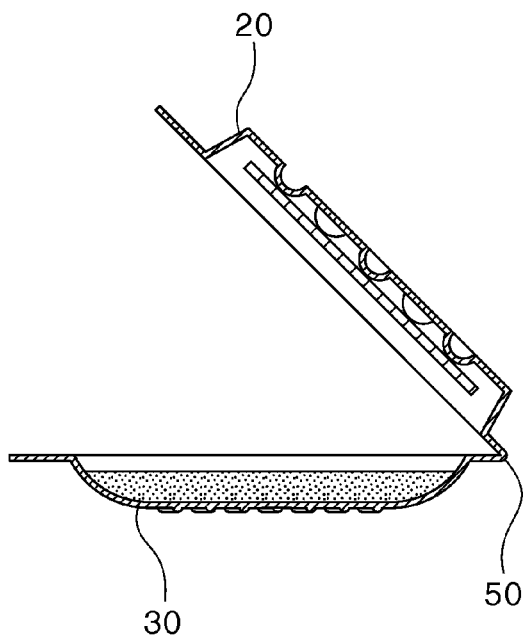
FIG. 4 is a sectional view of a preferred embodiment of the device of the present invention during preparation.

The device of the present invention is also for preparing the final pre-formed hydrogel product at-use in a suitable manner, namely, that is easy for the user to carry out. The final pre-formed hydrogel product is prepared at one of the compartments in which the interim components were originally packaged, preferably in the second compartment originally packaging the benefit component. The packaging of the present device comprises a means for contacting the pre-formed hydrogel component and benefit component upon use. FIG. 2 depicts a preferred embodiment of the present device with the seal liner (40) freshly removed. The pre-formed hydrogel component (21) is positioned in the first compartment (20) and the benefit component (31) is positioned in the second compartment (30). Referring back to FIG. 1, a notch area (50) runs through material separating the first and second compartments. Such notch area is for slightly weakening the material such that it can be folded without complete rupture by the user as depicted in FIG. 4. By such folding, the user may bring the pre-formed hydrogel component and benefit component in contact with each other without touching either the preformed hydrogel component or the benefit component. Such preparation is suitable from a hygiene point of view, as avoiding contamination from the hands. The overall configuration of the package is also suitable from a manufacturing cost point of view, as the package may be made with commonly used material and conventional thermoforming technology.

Figure 3:
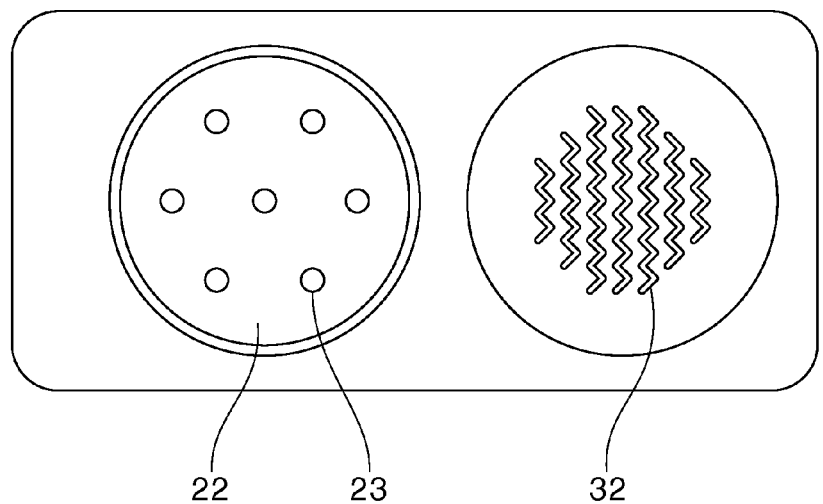
FIG. 3 is a perspective view of a preferred embodiment of the package of the present invention.
Figure 5:
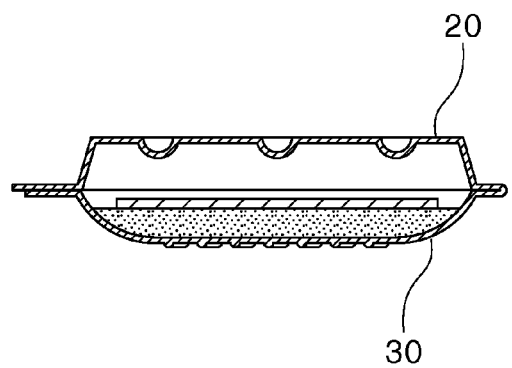
FIG. 5 is another sectional view of a preferred embodiment of the device of the present invention wherein preparation of a final product is completed.

In a preferred operational mode, the pre-formed hydrogel component is transferred from the first compartment to the second compartment as depicted in FIG. 4 and FIG. 5. The pre-formed hydrogel component thus transferred to the second compartment contacts the benefit component for providing the final hydrogel product, which may be retrieved by the user. The user may further engage or soak the pre-formed hydrogel component into the benefit component for better retrieval of the benefit component. Referring to FIG. 3, the interior surface (22) of the first compartment may comprise embossing (23) for facilitating release of the pre-formed hydrogel component upon transferring into the second compartment. The interior surface (32) of the second compartment may also comprise embossing for facilitating preparation of the final product, for example, avoiding the hydrogel to slip out of the second compartment when the user engages the hydrogel component in the benefit component.

Figure 6:
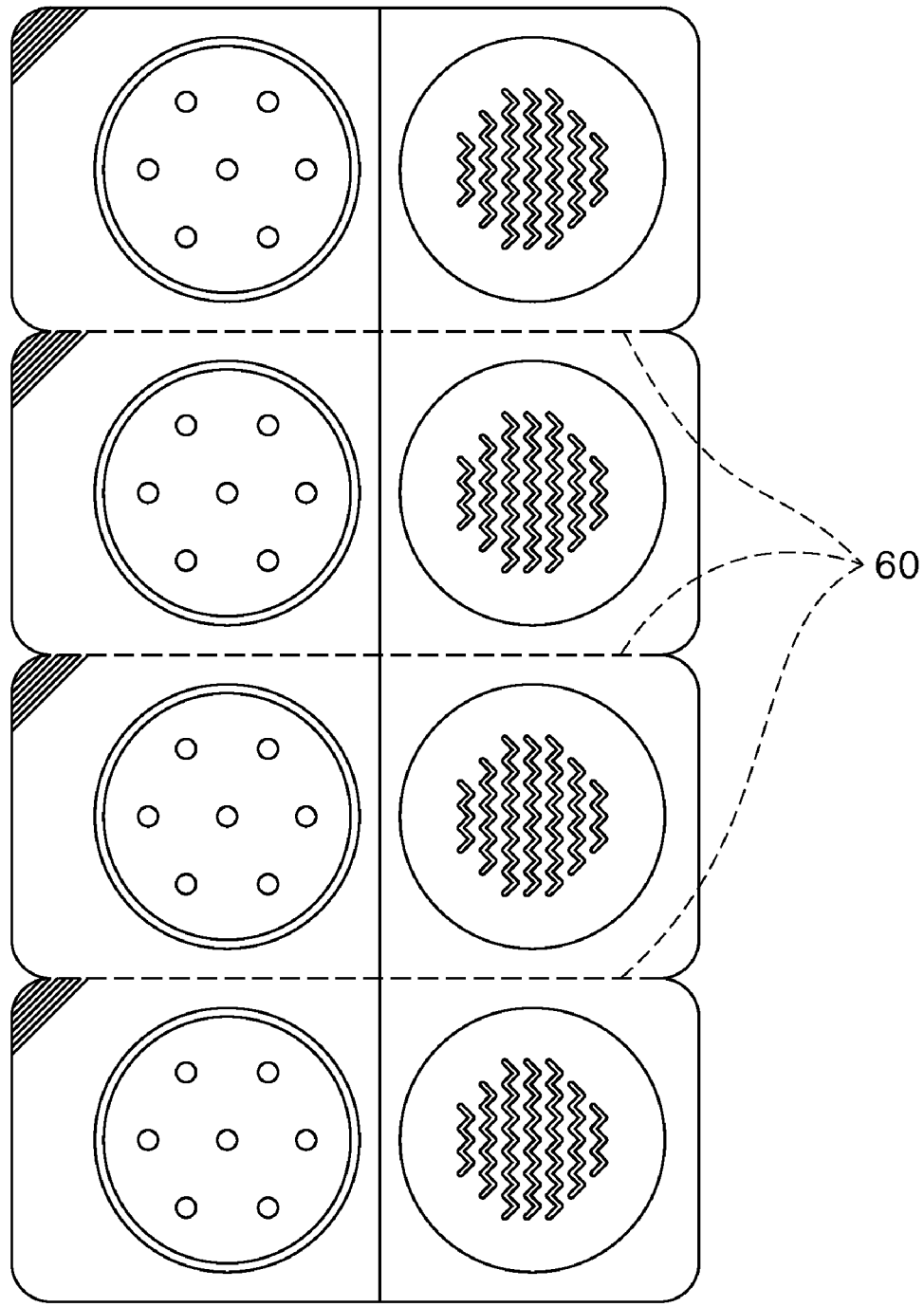
FIG. 6 is a perspective view of a preferred embodiment of the device of the present invention in a series of units.

The device of the present invention may be provided in individual units, or in a series of units as depicted in FIG. 6. The series of devices in FIG. 6 are provided in 4 doses/servings, wherein each unit can be separated away by breaking perforated areas (60). Providing a series of devices can be beneficial for providing doses designed to be administered in a fixed period of time, such as a day, and/or for simply reducing secondary packaging material.

Pre-Formed Hydrogel Component

The device of the present invention comprises a pre-formed hydrogel component. The preformed hydrogel component of the present invention provides structure and shape, allowing it to be handled and to suit treatment of a specific target area of the skin, hair or nails, fabric or hard surface, or to be orally administered or consumed. Physical characteristics such as strength, flexibility, and surface texture are designed to meet the function for which the pre-formed hydrogel component is intended to achieve.

For topical use, the pre-formed hydrogel may also act as a reservoir or as a delivery vehicle for skin benefit agents, drugs, or aesthetic cosmetic agents for the skin, hair, or nails. Further, when applied to the skin, hair or nails, by virtue of evaporation of a solvent, the pre-formed hydrogel may provide a cooling action to the object during use. In the foods or oral administered drugs area, the pre-formed hydrogel may provide a flavor, taste, nutrition, or certain pharmaceutical active. In the non-personal care area, it can also act as a reservoir or as a delivery vehicle for encompassing fabric or hard surface treating agents such as solvents for removing/absorbing stains, detersive surfactants, and bleaches. The pre-formed hydrogel may or may not have a supporting substrate.

Gelling Agent

The pre-formed hydrogels of the present invention comprises a gelling agent that provides structure and shape. The type and amount of gelling agent to be included in the pre-formed hydrogel is selected according to the desired characteristic and purpose of the product, depending on the properties of the gelling agent. Generally, more gelling agent will provide a more rigid pre-formed hydrogel. For providing food products or orally administrative products, the gelling agent must be edible and acceptable in taste and flavor. Many types of gelling agents are known in the art, including polymeric gellants and particulate based gellants such as various types of clays or other silicate based materials. Highly preferred herein are polymeric gelling agents that form 3-dimensional gel networks in combination with water. For providing cosmetic devices, the pre-formed hydrogel preferably comprises from about 0.5% to about 20%, more preferably from about 1% to about 10%, of gelling agent.

The gelling agents herein may be water soluble or water insoluble, and selected according to the solvent. When the solvent is water or water-based, preferably the gelling agent is water soluble. Water insoluble polymeric gellants such as silicone materials e.g. organopolysiloxane resins, or block copolymer thermoplastic elastomers, may be used in an appropriate solvent.

The water-soluble polymeric gellants for use in the present invention are selected from synthetic or natural polymers, and mixtures thereof. Preferred polymers for use herein are natural polymers, including gelatin, polysaccharides, and mixtures thereof. Preferred are polysaccharides. The term "polysaccharide" herein means a naturally occurring or synthetically produced, linear, branched or cross-linked polymer of monosaccharide units, which swells when dispersed in water at low concentrations and thickens the aqueous phase.

The polysaccharides for use in the pre-formed hydrogels herein are preferably selected from red seaweed polysaccharides; glucomannans; galactomannans; fermentation polysaccharides, or derivatives thereof; brown seaweed polysaccharides; extracts of marine invertebrates; starch, or derivatives thereof; natural fruit extracts; plant fiber derivatives; kelp; natural plant exudates; and resinous gums; or mixtures thereof. The total polysaccharide level is controlled so that other optional components of the preformed hydrogel are not as tightly bound within the gel network and are available for diffusion.

When gelatin is used in the pre-formed hydrogels herein, a high-molecular weight gelatin is combined with a low-molecular weight one to control the solubility. A gelatin having a low molecular weight of 20,000 or less has weaker gelling ability when used as the sole gelling agent.

Brown seaweed polysaccharides are isolated by extraction from various species of *Phaebophyceae*. Suitable brown seaweed polysaccharides for use herein include algin, alginic acid, ammonium alginate, calcium alginate, potassium alginate, sodium alginate, propylene glycol alginate, and mixtures thereof.

Red seaweed polysaccharides are isolated from marine plant species belonging to the class of Rhodophyceae. Red seaweed polysaccharides provide mechanical strength to the pre-formed hydrogel. Suitable red seaweed polysaccharides for use in the present invention include agar known in the industry under the (CTFA) trade designation as agar agar flake derived from various *Gelidium* plant species or closely related red algae commercially available as "Agar Agar 100" or "Agar Agar 150" from TIC Gums (Belcamp, Md., USA) or "Agar Agar K-100" from Gumix International Inc. (Fort Lee, N.J., USA); agarose commercially available as "Sea Plaque®" from FMC (Philadelphia, Pa., USA) and "Agarose Type 1-b" from Sigma—Aldrich Co. Ltd. (Poole, UK); carrageenan, comprising the fractions lambda-, iota- and kappa—which are the water extracts obtained from various members of the Gigartinaceae or Solieriaceae families, known in the industry under the (CTFA) trade designation as chondrus, commercially available as "Gelcarin® LA", "Seakem® 3/LCM", or "Viscarin® XLV", all from FMC (Philadelphia, Pa., USA); and furcellaran commercially available from Gum Technology Corporation (Tucson, Ariz., USA) and Continental Colloids Inc. (Chicago, Ill., USA), or mixtures thereof. Preferably, the red seaweed polysaccharide for use herein is selected from agar, agarose, kappa-carrageenan and furcellaran, or mixtures thereof.

Glucomannans are polysaccharides which comprise an essentially linear backbone of glucose and mannose residues. Glucomannans have short side branches attached to the linear backbone and acetyl groups are randomly present at the C-6 position of a sugar unit. The acetyl groups are generally found on one per six sugar units to one per twenty sugar units. Suitable glucomannans or derivatives thereof for use herein have a ratio of mannose to glucose of from about 0.2 to about 3. Preferred glucomannans for use herein include konjac mannan, which is the generic name for the flour formed from grinding the tuber root of the *Amorphophallus konjac* plant (elephant yam), commercially available under the trade name "Nutricol® konjac flour" from FMC (Philadelphia, Pa., USA); and deacetylated konjac mannan; or mixtures thereof.

Galactomannans are vegetable reserve polysaccharides which occur in the endosperm cells of numerous seeds of Leguminosae. The collective term "galactomannan" comprises all polysaccharides which are built up of galactose and mannose residues. Galactomannans comprise a linear backbone of $(1{\rightarrow}4)$-linked $\beta$-D-mannopyranosyl units. To these rings are attached as branches, isolated galactopyranose residues by $\alpha$-$(1,6)$-glucoside bonds. Galactomannans may in addition also contain minor amounts of other sugar residues. Suitable galactomannans for use herein are fenugreek gum; lucern; clover; locust bean gum known for example in the industry under the (CTFA) trade designation as carob bean gum, commercially available as "Seagul L" from FMC (Philadelphia, Pa., USA); tara gum commercially available from Starlight Products (Rouen, France) or Bunge Foods (Atlanta, Ga., USA); guar gum derived from the ground endosperms of *Cyamopsis tetragonolobus*, commercially available as "Burtonite V7E" from TIC Gums (Belcamp, Md., USA), "Jaguar C" from Rhone-Poulenc (Marietta, Ga., USA), or "Supercol" from Aqualon (Wilmington, Del., USA); and cassia gum commercially available from Starlight Products (Rouen, France), or mixtures thereof. Preferably, the galactomannans for use herein have an average one of every 1 to about 5 mannosyl units substituted with a $(1{\rightarrow}6)$-linked-$\alpha$-D-galactopyranosyl unit and are selected from guar gum, locust bean gum and cassia gum, or mixtures thereof.

Fermentation polysaccharides are polysaccharides which are commercially produced by the fermentation of microorganisms in a medium containing a carbon and nitrogen source, buffering agent, and trace elements. Suitable fermentation polysaccharides or derivatives thereof, for use in the present invention include gellan gum known in the industry under the (CTFA) trade designation as gum gellan, a high molecular weight hetero polysaccharide gum produced by a pure-culture fermentation of a carbohydrate with *Pseudomonas elodea*, commercially available as "Kelcogel" from Kelco (San Diego, Calif., USA); xanthan gum which is a high molecular weight hetero polysaccharide gum produced by a pure-culture fermentation of a carbohydrate with *Xanthomonas campestris*, known in the industry under the (CTFA) trade designation as xanthan, commercially available for example as "Keltrol CG 1000/BT/F/GM/RD/SF/T/TF", from Calgon (Pittsburgh, Pa., USA), or "Kelzan" from Kelco (San Diego, Calif., USA); natto gum; pullulan; rhamsan gum; curdlan;

succinoglycan; welan gum; dextran, commercially available as "Sephadex G-25" from Pharmacia Fine Chemicals (Piscataway, N.J., USA) and derivatives thereof; and sclerotium gum, commercially available as "Amigel" from Alban Muller International (Montreil, France), or mixtures thereof. Preferred fermentation polysaccharides or derivatives thereof are selected from gellan gum and xanthan gum, or mixtures thereof. More preferably the fermentation polysaccharide or derivative thereof is xanthan gum.

Extracts of marine invertebrates can also be used. Polysaccharides derived from marine invertebrates, specifically the exoskeleton of such invertebrates, consist chiefly of N-acetyl-D-glucosamine residues. Examples of such polysaccharides suitable for use herein include chitosan, commercially available for example as "Marine Dew" from Ajinomoto (Teakneck, N.J., USA); and hydroxypropyl chitosan commercially available for example as "HPCH Liquid" from Ichimaru Pharcos (Yamagata Gun Gifu-Pref, Japan) and derivatives; or mixtures thereof.

Starches are polysaccharides which consist of various proportions of two glucose polymers, amylose and amylopectin. Suitable materials for use herein include starch, amylopectin and dextrin, commercially available as "Nadex 360" from National Starch (Bridgewater, N.J., USA), and derivatives or mixtures thereof. Examples of natural fruit extracts suitable for use herein include pectin, arabian and mixtures thereof. A suitable example of a plant fiber derivative for use herein is cellulose. Suitable polysaccharides obtained from natural plant exudates for use herein include karaya, tragacanth, arabic, tamarind, and ghatty gums, or mixtures thereof. Examples of resinous gums suitable for use herein include shellac gum, which is obtained from the resinous secretion of the insect *Laccifer (Tachardia) lacca*, damar gum; copal gum and rosin gum; or mixtures thereof.

Natural and synthetic polymeric gelling agents that form gels in combination with other substances, may also be used as a gelling agent in combination with other thermo-forming gelling agents, so long as the gel phase forming can been synchronized. They may be chemically cross linked. Some gelling agents form gels in combination with substances such as sugar, alcohol, or mono- or multi-valent salts. Mono- or multi-valent salts may additionally act as gel strengthening agents imparting added strength to the pre-formed hydrogels herein. Suitable cations for such salts can be selected from potassium, sodium, ammonium, zinc, aluminium, calcium and magnesium ions, or mixtures thereof. Suitable anions associated with the aforementioned cations may be selected from chloride, citrates, sulfate, carbonate, borate and phosphate anions, or mixtures thereof.

The water-soluble polymeric gellants for use in the present invention are selected from synthetic or natural polymers, and mixtures thereof. In general, the pre-formed, gel sheets of the present invention comprise less than 50%, more preferably less than 30% and especially less than 20% by total weight of a water-soluble polymeric gellant. Suitable synthetic polymers for use herein include non-ionic water-soluble polymers, acrylic acid based polymers, cellulose derivatives, and mixtures thereof.

A particularly preferred synthetic polymer system is disclosed in WO 00/06215, incorporated herein by reference, which describes a product suitable for attaching biomedical devices to the skin. In particular the document discloses a bioadhesive, hydrogel composition comprising an aqueous plasticiser, a polymer of one or more monomers comprising a hydrophilic unsaturated water soluble acrylamido monomer, particularly NaAMPS, and a hydrophobic polymer, such as an ethylene/vinyl acetate copolymer.

Physical cross linking refers to polymers having cross links which are not chemical covalent bonds but are of a physical nature such that there are areas having high crystallinity or areas having a high glass transition temperature. Such cross linked polymers may also be used. Preferably, the polymer is chemically cross linked thermally. In addition when chemical cross links are formed in the system, a polyfunctional cross linker and/or a free radical initiator may be present in the premix to initiate the cross linking upon irradiation.

Preferably, the pre-formed hydrogels herein comprise a mixture of water-soluble polymeric gelling agents of natural origin. A preferred water-soluble polymeric gelling agent mixture herein may comprise a polysaccharide and a non-ionic water-soluble polymer or, alternatively, it may comprise two polysaccharides. More preferably, the water-soluble polymeric gel forming agent is a polysaccharide mixture, wherein the polysaccharide mixture comprises (1) at least one red seaweed polysaccharide; brown seaweed polysaccharide; or mixtures thereof; and (2) at least one fermentation polysaccharide; galactomannan; glucomannan; natural plant exudate; or natural fruit extract; and derivatives or mixtures thereof. Even more preferably, the water-soluble polymeric gel forming agent of the pre-formed hydrogels of the present invention is a polysaccharide mixture comprising (1) at least one red seaweed polysaccharide; and (2) at least one fermentation polysaccharide; glucomannan; or galactomannan; and derivatives or mixtures thereof.

In a preferred embodiment for providing a pre-formed hydrogel free of supporting substrate, the water-soluble polymeric gel forming agent of the present invention is a polysaccharide mixture, comprising a red seaweed polysaccharide and a glucomannan or a galactomannan. The ratio of red seaweed polysaccharide to glucomannan or galactomannan in the polysaccharide mixture is preferably from about 20:1 to about 1:5 and more preferably from about 10:1 to about 1:2. Without being limited by theory, it is believed that gel compositions herein form 3-dimensional networks or matrices which bind or encapsulate other ingredients of the composition.

Solvent

The pre-formed hydrogels of the present invention comprise a solvent for the gelling agent, which may be water, water solutions, or water dispersions. Typically the gelling agent is at least miscible in the solvent at sol phase state for eventually providing a uniform unilamellar pre-formed hydrogel. The amount and type of solvent is determined to provide a stable gel phase with the gelling agent, in view of the desired mechanical properties, particularly gel strength and flexibility, and also in view of the desired characteristic of the obtained product. Preferably, the solvent further acts as a plasticiser or softener for the pre-formed hydrogel.

For topical use, the pre-formed hydrogel comprises a hydrophilic solvent. The term "hydrophilic" as used in reference to solvents herein, means that the solvent is miscible with water, at least in a solvent to water ratio of 1 to 10, preferably 1 to 5. A topical acceptable, hydrophilic solvent is one which can be used in a pre-formed hydrogel to be applied against the skin without causing irritation and which is miscible with water. Suitable hydrophilic solvents include lower alcohols such as ethanol, and polyhydric alcohols such as propylene glycol, butylene glycol, hexylene glycol, glycerin, sorbitol; polyethylene glycols of MW less than 30,000, preferably less than 10,000; and polypropylene glycols of MW less than 5,000, preferably less than 1,000. Advantageously, many of the polyhydric alcohols useful as hydrophilic solvents herein also function as humectants for the skin. Further, the hydrophilic solvent can assist in diffusion of skin benefit agents to the skin and, by evaporation from the pre-formed hydrogel, can also provide cooling, making the pre-formed hydrogel more comfortable to wear. Preferred in this latter respect are solvents which are liquid at 25° C. For topical use, preferably the solvent comprises water and at least one polyhydric alcohol, more preferably, the solvent consists essentially of water and polyhydric alcohol. In a preferred embodiment, the pre-formed hydrogel comprises from about 10% to about 99.5% of water, more preferably from about 20% to about 95%, and yet more preferably from about 30% to about 90% of water. Still preferably, the pre-formed hydrogel further comprises from about 1.0% to about 50%, preferably from about 5% to about 45%, more preferably from about 10% to about 40% of polyhydric alcohol.

For oral administration use, the solvent is selected from the group hereinabove that are safe, and preferably pleasing, for oral consumption.

Benefit Component

The device of the present invention comprises a benefit component. The benefit component of the present invention provides additional benefit to the pre-formed hydrogel component when contacted upon use, however comprises at least one compound that is unstable when brought in contact with the pre-formed hydrogel component. Thus, the final hydrogel product is prepared at-use. The benefit component may be in the form of liquid, powder, or solid, preferably liquid or powder. The benefit component may comprise a compound that enhances synerisis, enhances stiffening, or produces unaesthetic color, taste, flavor, and/or odor when contacted with the pre-formed hydrogel component. The benefit component may comprise an interim compound or catalyst which reacts with water encompassed in the pre-formed hydrogel component. The benefit component may comprise a compound that quickly alters its physical properties or decreases its performance by being easily dissolved/absorbed in the pre-formed hydrogel component, or absorbing the solvent from the pre-formed hydrogel component.

Compounds which are known to be unstable with the pre-formed hydrogel component, particularly with water, and thus suitable for comprising in the benefit component are, for example, easily oxidated water-soluble compounds, heat generating compounds, powder compounds, electrically charged compounds, gas forming compounds, and mixtures thereof. The unstable compounds herein may be categorized or described by their chemical/physical property or their postulated mode of action. However, it is to be understood that the unstable compound herein can, in some instances, provide more than one benefit or operate via more than one mode of action. Therefore, classifications herein are made for the sake of convenience and are not intended to limit a compound to the particularly stated characteristic.

Easily oxidated water-soluble compounds herein include ascorbic acid compounds. While ascorbic acid compounds are useful for topical use and oral consumption, they may provide visible yellowness to the pre-formed hydrogel when in contact for over about 5 days. Ascorbic acid compounds provide skin lightening benefit when used topically, and provide distinctive flavor when taken orally. Ascorbic acid compounds useful herein include, ascorbic acid per se in the L-form, ascorbic acid salt, and derivatives thereof. Ascorbic acid salts useful herein include, sodium, potassium, lithium, calcium, magnesium, barium, ammonium and protamine salts. Ascorbic acid derivatives useful herein includes, for example, esters of ascorbic acid, and ester salts of ascorbic acid. Particularly preferred ascorbic acid compounds include 2-o-D-glucopyranosyl-L-ascorbic acid, which is an ester of ascorbic acid and glucose and usually referred to as L-ascorbic acid 2-glucoside or ascorbyl glucoside, and its metal salts, and L-ascorbic acid phosphate ester salts such as sodium ascorbyl phosphate, potassium ascorbyl phosphate, magnesium ascorbyl phosphate, and calcium ascorbyl phosphate. Commercially available ascorbic compounds include magnesium ascorbyl phosphate available from Showa Denko, 2-o-D-glucopyranosyl-L-ascorbic acid available from Hayashibara and sodium L-ascorbyl phosphate with tradename STAY C available from Roche.

Heat generating compounds herein include those which generate heat upon contact with abundant air when breaking the seal for preparation, and/or upon contact with water included in the hydrogel component. Generation of heat may provide a pleasant warm feeling when used topically, and may further enhance penetration of active ingredients included in the hydrogel component and/or the benefit component. Suitable heat generating compounds include, for example, chlorides such as calcium chloride ($CaCl_2$, $CaCl_2.H_2O$, $CaCl_2.2H_2O$), magnesium chloride ($MgCl_2$, $MgCl_2.2H_2O$, $MgCl_2.4H_2O$), aluminum chloride ($AlCl_3$, $AlCl_3.6H_2O$), ferric chloride ($FeCl_3$, $FeCl_3.2H_2O$), and zinc chloride ($ZnCl_2$); sulfates such as magnesium sulfate ($MgSO_4$, $MgSO_4.H_2O$, $MgSO_4.4H_2O$), zinc sulfate ($ZnSO_4.H_2O$), ferrous sulfate ($FeSO_4$, $FeSO_4.H_2O$), aluminum sulfate ($Al(SO_4)_3$), calcium sulfate ($CaSO_4$, $CaSO_4.\frac{1}{2}H_2O$, $CaSO_4.H_2O$), and sodium sulfate ($Na_2SO_4$); dry alum; calcium oxide (CaO); magnesium oxide (MgO); sodium carbonate ($Na_2CO_3$); iron oxide: zinc oxide; zeolite; and sodium hydrogenphosphate ($Na_2HPO_4$). Preferred are anhydrous inorganic salts such as sodium sulfate ($Na_2SO_4$), calcium sulfate ($CaSO_4$), magnesium sulfate ($MgSO_4$), aluminum sulfate ($Al(SO_4)_3$), calcium chloride ($CaCl_2$), magnesium chloride ($MgCl_2$), calcium oxide (CaO), and mixtures thereof, in view of their effective heat generation, mildness to hair and/or skin, and easy handling. More preferred is anhydrous magnesium sulfate ($MgSO_4$). The heat generating compounds useful herein have an average diameter of, preferably from about 0.01 µm to about 40 µm, more preferably from about 0.05 µm to about 30 µm, still more preferably from about 0.1 µm to about 20 µm, in view of preventing gritty feel upon handling or when topically applied.

Powder compounds herein typically quickly alters its physical properties or decreases its performance by being easily dissolved/absorbed in the pre-formed hydrogel component, or absorbing the solvent from the pre-formed hydrogel component. Powder compounds may be any that provide a topical benefit or are pleasing for oral consumption. Powder compounds for topical use herein include those which provide a distinctive skin feel, such as titanium dioxide, talc, cellulose powder, iron oxide, silicone resins, ferric oxide, zinc oxide, and others. Powder compounds for oral consumption herein include, for example, salt, sugar, pepper, rice powder, cellulose powder, starch powder, cocoa powder, soya bean powder, wheat flour, and others.

Electrically charged compounds such as electrolytes and ionic surfactants are useful compounds for detersive purposes, however, may enhance synerisis or even decompose the pre-formed hydrogel when in contact. Electrically charged compounds herein include, for example, any electrolyte which provides alkali metal or alkali earth metal ions, anionic surfactants, cationic surfactants, anionic polymers, cationic polymers, and others.

Gas forming compounds useful herein are those which provide any kind of effervescent effect when contacted with solvent, typically water. Gas forming compounds may be suitable for any product to provide a visible, audible, or olfactory signal that a final product is being made. The gas forming compounds may enhance taste and flavor, enhance topical absorbance, or enhance detersive effect. Useful herein are alkaline salts which generate carbon dioxide upon dissolution with water, including sodium carbonate, sodium hydrogen carbonate, sodium sesquicarbonate, potassium carbonate, potassium hydrogen carbonate, potassium sesquicarbonate, and mixtures thereof. When such alkaline salts are used, it is preferable to further comprise organic acids or its salts to regulate the pH of the final hydrogel product. Suitable organic acids for this use include aliphatic carboxylic acids such as citric acid, tartaric acid, malic acid, oxalic acid, malonic acid, succinic acid, glutaric acid, adipic acid, fumaric acid, and maleic acid, aromatic carboxylic acids such as benzoic acid, phthalic acid, isophthalic acid, terephthalic acid, and cinnamic acid, heterocyclic carboxylic acids such as nicotinic acids, acidic amino acid such as glutamic acid and aspartic acid, and mixtures thereof. Also useful herein are particles which contain pressurized gas trapped within the particles.

Products for Topical Use

In a highly preferred embodiment, the final pre-formed hydrogel product of the present invention is a sheet-like patch useful for delivering skin benefit agents to the skin, hair, or nails. The products are generally of a size such that each surface has an area of from about 0.25 $cm^2$ to about 1,000 $cm^2$, preferably from about 1 $cm^2$ to about 400 $cm^2$. Surface area refers to that of a flat plane having the same boundary as the surface i.e. ignoring any surface texturing, when present. The pre-formed hydrogel herein can be, for example, square, circular, semicircular, rectangular, oval, rings, crescents, teardrops or other more complex shapes which may be composites of these, for covering areas such as the eye area, eye lids, the nose, the mouth area, the forehead, the cheek, the chin, the entire contour of the face, neck, arm, other specific places of the body, or combinations thereof. The pre-formed hydrogel should be flexible enough to fit along the surface of the skin on which it is applied. Yet, minimum gel strength is required so that the pre-formed hydrogel does not rupture under its own weight when overhanging, for example, when the user wears the product.

The present invention further relates to a final pre-formed hydrogel product comprising:

(1) a pre-formed hydrogel component comprising:
  (a) from about 10% to about 99.5% water; and
  (b) from about 0.5% to about 20% polysaccharide gelling agent;
wherein the pre-formed hydrogel component is free of a supporting substrate, has a thickness of from about 0.1 mm to about 5 mm, preferably from about 0.5 mm to about 2.0 mm and a first surface and a second surface, the first surface having a repeating texture having a depth of from about 10 μm to about 500 μm, preferably from about 50 μm to about 200 μm at a frequency of from about 0.2 to about 1 per mm, preferably from about 0.3 to about 0.7 per mm; wherein the depth of the texture is at least about 10% of the thickness of the pre-formed hydrogel component; and (2) a benefit component comprising a skin benefit agent and having a viscosity of from about 1000 mPa·s to about 100,000 mPa·s, preferably from about 5000 mPa·s to about 300,000 mPa·s;
wherein the repeating texture is so designed to provide a network of channels that allows fluid communication of the benefit component when the first surface is worn on the skin. The term "first surface" as used herein, means a surface of the pre-formed hydrogel to be worn on the skin, and which faces the seal when packaged in the first compartment.

The term "thickness" as used herein, means a thickness of a pre-formed hydrogel component, wherein when the sheet is textured, the peaks of the texture are used for measuring the thickness.

The term "depth" as used herein, relates to a length in the thickness direction of a texture provided on the surface of a pre-formed hydrogel component.

The term "frequency" as used herein, relates to the number of repeating non-planar topography per mm, the repetition of the non-planer topography providing a texture to the surface of a pre-formed sheet.

The pre-formed hydrogel component of the present invention having a certain thickness and texture of certain depth and frequency to the first surface provides various benefits for the user. The first surface is positioned to face the seal when packaged in the first compartment, so that when the pre-formed hydrogel component is transferred into the second compartment, the first surface contacts directly with the benefit component, and thus the user is derived to apply such surface on the skin. In one highly preferred embodiment, the benefit component is in such amount and viscosity that it covers only the first surface of the pre-formed hydrogel, as depicted in FIG. 5.

The final pre-formed hydrogel product comprises a benefit component which facilitates convenient adhesion of the product to the skin by applying the first surface to the skin. After the hydrogel product is worn on the skin, the benefit component immediately evenly distributes throughout the area on which the product is worn, leaving the discontinuous, spaced wearer contacting areas more or less vacuum. Thus, the product is sucked onto the skin. For such effective sucking of the product on the skin, the pre-formed hydrogel component is preferably uniform in thickness. The channels further provide a reservoir of the benefit component between the pre-formed hydrogel component and the skin, thus allowing continuous contact of the benefit component to the skin. With the dimensions above, the hydrogel product provides adequate adhesion to the skin such that, even when worn in a vertical manner, the product does not easily drag down the skin.

The benefit component may be aqueous solutions, including gels, or emulsions such as oil-in-water emulsions, water-in-oil emulsions or multiple emulsions having aqueous or oily external phases, all of which have a viscosity of between about 1000 mPa·s and about 100,000 mPa·s. The viscosity of the coating composition is measured on a Brookfield viscometer using a heliopath T-bar C spindle at 5 rpm.

The weight ratio of the benefit component to the pre-formed hydrogel component is generally more than about 1:50, preferably from about 1:25, more preferably from about 1:15 to about 10:1.

The pre-formed hydrogel component herein can be made by any suitable process, preferably, by a cooling process utilizing the gel transition point of the gelling agent. Other processes include injection molding.

In one highly preferred embodiment, the benefit component comprises a safe and effective amount, preferably from about 0.1% to about 10% ascorbic acid compound for providing chronic skin lightening benefit to the skin.

Skin Benefit Agents

In a highly preferred embodiment, the benefit component is a liquid composition comprising at least one skin benefit agent for the skin, hair or nails. Preferably, the pre-formed hydrogel component and the benefit component each comprise at least one skin benefit agent in common. For purposes of the present invention, the skin benefit agents discussed in this section herein exclude those compounds that are unstable with the pre-formed hydrogel component.

When a common skin benefit agent is included, the benefit component can rapidly provide a skin benefit agent to the target area upon use, while the pre-formed hydrogel can act as a reservoir for the skin benefit agent or inhibit the pre-formed hydrogel from absorbing the skin benefit agent from the benefit component.

The term "skin benefit agent" as used herein, means an active ingredient which provides a cosmetic and/or therapeutic effect to the area of application on the skin, hair, or nails. The skin benefit agents useful herein include anti-acne agents, emollients, non-steroidal anti-inflammatory agents, topical anaesthetics, artificial tanning agents, antiseptics, anti-microbial and anti-fungal actives, skin soothing agents, sunscreening agents, skin barrier repair agents, anti-wrinkle agents, anti-skin atrophy actives, lipids, skin lightening agents, sebum inhibitors, sebum inhibitors, skin sensates, protease inhibitors, skin tightening agents, anti-itch agents, hair growth inhibitors, desquamation enzyme enhancers, anti-glycation agents, and mixtures thereof.

Preferably, the benefit component of the present invention comprise from about 0.01% to about 60%, preferably from about 0.1% to about 40% and most preferably from about 0.5% to about 30% by weight of the benefit component of at least one skin benefit agent, or mixtures thereof.

Preferred examples of skin benefit agents useful herein include those selected from the group consisting of: salicylic acid, niacinamide, panthenol, tocopheryl nicotinate, benzoyl peroxide, 3-hydroxy benzoic acid, flavonoids (e.g., flavanone, chalcone), farnesol, phytantriol, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, retinyl esters (e.g., retinyl propionate), phytic acid, N-acetyl-L-cysteine, lipoic acid, tocopherol and its esters (e.g., tocopheryl acetate), azelaic acid, arachidonic acid, tetracycline, ibuprofen, naproxen, ketoprofen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline, and mixtures thereof.

For cosmetic methods of treatment of the skin, hair or nails, the cosmetic skin benefit agent is preferably selected from anti-wrinkle and anti-skin atrophy actives, anti-acne actives, artificial tanning agents and accelerators, emollients, humectants, skin repair actives, skin barrier repair aids, skin lightening agents, skin sensates, skin soothing agents, lipids, sebum inhibitors, sebum stimulators, sunscreening agents, protease inhibitors, skin tightening agents, anti-itch ingredients, and desquamation enzyme enhancers, or mixtures thereof.

The pH of the pre-formed hydrogel component and the benefit component herein is preferably from about 3 to about 9, more preferably from about 4 to about 8. The pH may be selected depending on the activity of the skin benefit agent.

Depending on the skin benefit agent contained therein, the final pre-formed hydrogel product of the present invention may have at least one of the following uses; hydrating the skin, hair or nails, smoothing fine lines and wrinkles; cosmetically treating acne; firming or softening the skin, strengthening; softening; exfoliating; improving and/or evening skin tone and/or texture; skin, hair or nail lightening; tanning; reducing the appearance of pores; absorbing or controlling secretions; protecting and/or soothing the skin, hair or nails, muscles, aches or pains; reducing puffiness, and/or dark circles; stimulating wound healing; warming, refreshing or cooling the skin, hair or nails; relieving inflammation; brightening the complexion; decongesting; reducing swelling; treating dermatological conditions; cushioning; purifying; fragrancing; reducing bacterial or micro-organism growth; healing; repelling insects; removing unwanted hair, dirt, or make-up; and coloring or bleaching the target area to which the final pre-formed hydrogel product is applied.

Method of Use

The final hydrogel product of the present invention is prepared shortly prior to wearing on the skin, preferably within about 10 minutes, according to the preparation steps as described above. The first surface of the final hydrogel product is worn on the skin so that a network of channels provided by the surface texture allows fluid communication of the benefit component. The final hydrogel product thus obtained is applied to a target area of the skin, hair or nails, and will generally be left on the target area for about 1 minute to about 12 hours, preferably about 5 to about 60 minutes.

EXAMPLES

The following examples further describe and demonstrate the preferred embodiments within the scope of the present invention. The examples are given solely for the purpose of illustration, and are not to be construed as limitations of the present invention since many variations thereof are possible without departing from its spirit and scope.

The preparation-at-use devices are made of components having the following compositions and formed by the process described herein:

TABLE 1

Compositions 1-6 for Hydrogel Component
For providing a formed structure, Examples
4-6 further comprise a supportive layer.

| Ingredient (weight percentage) | Ex. 1 | Ex. 2 | Ex. 3 | Ex. 4 | Ex. 5 | Ex. 6 |
|---|---|---|---|---|---|---|
| Agarose | 0.3 | 0.8 | 1.5 | | | |
| Agar | 0.60 | | | | | |
| Kelgum (Kelco)[1] | | 0.5 | 0.75 | | | |
| Keltrol T (Kelco)[1] | 0.2 | | | | | |
| Locust Bean Gum | 0.2 | | | | | |
| NaAMPS[7] | | | | 32.5 | | |
| Darocure PI[8] | | | | 0.075 | | |
| IRR210 XL[9] | | | | 0.075 | | |
| Sodium Polyacrylate | | | | | 12.0 | 7.0 |
| Sodium Carboxymethylcellulose | | | | | | 4.0 |
| Alminum Hydroxide | | | | | 0.1 | 0.1 |
| Niacinamide | | 5.0 | 10.0 | 2.0 | 2.0 | |
| Sodium Salicylate | | | | | | 0.10 |
| Dl-menthol | | | | | | 0.01 |
| D-Panthenol | 5.0 | | 1.0 | | | |
| Glycerin | 10.0 | 15.0 | 10.0 | 32.5 | 35.0 | 30.0 |
| Tartaric Acid | | | | | 0.3 | |
| Kaolin | | | | | 3.0 | 3.0 |
| Disodium EDTA | | 0.10 | 0.10 | | 0.10 | 0.10 |
| Butylene Glycol | | 5.0 | 5.0 | | | |
| Hexylene Glycol | 3.0 | | | | | |
| Ethyl Paraben | 0.20 | 0.15 | 0.15 | | | |
| Water | | | | to 100% | | |

TABLE 2

Compositions 7-11 for Benefit Component

| Ingredient (weight percentage) | Ex. 7 | Ex. 8 | Ex. 9 | Ex. 10 | Ex. 11 |
|---|---|---|---|---|---|
| Kelgum (Kelco)[1] | 0.1 | | | | |
| Keltrol T (Kelco)[1] | | 0.5 | 0.9 | | 1.1 |
| Locust bean gum | 0.4 | | | | |
| Polyacrylamide, isoparaffin & laureth-7 | | | | 2.75 | |
| Niacinamide | 5.0 | | 8.0 | 3.5 | 10.0 |
| Ascorbil Glucoside | | 2.0 | 2.0 | | 2.0 |
| Sodium Metabisulfite | | | 0.02 | | 0.03 |
| D-Panthenol | | 5.0 | 2.0 | 2.0 | 1.0 |
| Glycerin | | 5.0 | 10.0 | 9.0 | 10.0 |
| Disodium EDTA | 0.10 | 0.1 | 0.1 | 0.1 | 0.1 |
| Butylene glycol | | 5.0 | | | 5.0 |
| Hexylene glycol | | 5.0 | | | |
| Pentylene Glycol | | | | | 2.0 |
| Tospearl ™ 145[2] | | | 6.0 | 1.0 | 7.5 |
| DC 2-1559 emulsion[3] | | | 3.0 | 4.0 | 3.0 |
| Magnesium ascorbyl phosphate | 3.0 | | | 3.0 | |
| Tocopheryl acetate | 0.5 | | | 0.75 | |
| PEG-60 hydrogenated castor oil | 1.50 | | | | |
| Cetyl alcohol | | | | 1.5 | |
| Stearyl alcohol | | | | 1.0 | |
| Lonzaine ™ 16SP[4] | 0.47 | | | | |
| Tinoderm ™ E[5] | | | | 10.0 | |
| Sucrose cocoate and sorbitan stearate[6] | | | | 1.0 | |
| Sodium Hydroxide | | 0.25 | 0.25 | | 0.25 |
| Yeast Ferment Filtrate[10] | | | 20.0 | | 10.0 |
| Water | | | | to 100% | |

TABLE 3

Composition 12 for Benefit Component

| Ingredient (weight percentage) | Example 12 |
|---|---|
| Niacinamide | 3.5 |
| Mica | 45.0 |
| Titanium Dioxide | 7.0 |
| Iron Dioxide | 1.5 |
| Squalane | 5.0 |
| Cetyl Isooctanoate | 3.0 |
| Glyceryl Isooctanoate | 7.0 |
| Talc | to 100% |

1 Kelgum and Keltrol T are, respectively, a 1:1 mixture of xanthan gum and locust bean gum; and xanthan gum, supplied by Kelco. San Diego, Calif., USA.

2 Polymethylsilsesquioxane from Toshiba

3 Dimethicone, dimelhiconol, laureth-4, laureth-23, and water; from Dow Corning

4 Water and celyl belaine from Lonza

5 Water, tocopheryl acetate, polysorbate 80, caprylic/capric triglyceride and lecithin from CIBA 6 Arlatone 2121 from ICI 7 NaAMPS from Lubrizol.

8 Darocure PI from Ciba Geigy.

9 IRR 210XL from UCB chemicals.

10 Yeast Ferment Filtrate: SKII Pitera available from Kashiwayama

Preparation of Device

The preparation-at-use device herein is made by any suitable process known in the art. The hydrogel components of Examples 1-6 may be combined with any benefit components of Examples 7-12 for providing a product for topical use. Products comprising Examples 7-11 as the benefit component are particularly useful for skin care products. Products comprising Examples 12 as the benefit component are particularly useful as a powder foundation product.

Preferably the present device is made by a continuous line process, wherein the pre-formed hydrogel component is made comprising the steps of:

(1) providing a sol phase composition of the pre-formed hydrogel component heated to a temperature of at least 5° C. higher than the sol-gel transition point;

(2) pre-cooling the sol phase composition to a temperature of between 0° C. and 5° C. higher than the sol-gel transition point;

(1) forming surfaces by pressing the sol phase composition between two liners, the two liners being supplied by two counter-rotating rollers facing each other, wherein the rollers further comprise cooling means;

(4) cooling the sol phase composition into a gel phase by cooling to no higher than 20° C.; and (5) cutting the gel phase composition by a die.

Packaging made by polypropylene having configurations shown in FIG. 3 and a seal component made by aluminum laminated with polyethyleneterephthalate on the outside and polypropylene on the inside are provided.

The preformed hydrogel component as obtained above is further transferred to a process for providing the present device comprising the steps of:

(6) providing a series of unsealed packages, each package unit having a first compartment and a second compartment;

(7) applying the benefit component in the second compartment of the package;

(8) placing the pre-formed hydrogel component in the first compartment of the package;

(9) sealing the package;

(10) providing a notch in the packaging material separating the first compartment and the second compartment; and

(11) providing a perforation for separating each unit device.

Preparation of Final Product at-Use

The final pre-formed hydrogel product is obtained by opening the seal, folding the packaging at the notch, and transferring the pre-formed hydrogel component into the second compartment to contact the benefit component.

The product thus obtained is applied to a target area of the skin.

When a product made of the combination of any of Examples 1-3 with any of Examples 7-11 are applied to the facial skin twice a day, at least 15 minutes for each application, and over a period of at least 2 weeks, chronic skin lightening benefit is provided. Such products further provide reduction of wrinkles/fine lines, texture improvement, and skin moisturization.

It is understood that the foregoing detailed description of examples and embodiments of the present invention are given merely by way of illustration, and that numerous modifications and variations may become apparent to those skilled in the art without departing from the spirit and scope of the invention; and such apparent modifications and variations are to be included in the scope of the appended claims.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of preparing a preparation-at-use device for delivering a benefit compound comprising the steps of:
   a. providing the device comprising:
      i. a sheet material having a first compartment and a second compartment distant from the first compartment, an area of weakness positioned between the first compartment and second compartment, and a releasable liner sealing the first compartment and second compartment;
      ii. a pre-formed hydrogel component in the first compartment; wherein the pre-formed hydrogel component comprises a gelling agent and a solvent; and
      iii. a benefit component in the second compartment;
   b. removing the releasable liner sealing the first compartment and second compartment; and
   c. folding the sheet material along the area of weakness to transfer the pre-formed hydrogel from the first compartment into the second compartment.

2. The method of claim 1 wherein the benefit component is selected from oxidated water-soluble compounds, heat generating compounds, powder compounds, electrically charged compounds, gas forming compounds, and mixtures thereof.

3. The method of claim 2 wherein oxidated water-soluble compounds are ascorbic acid compounds.

4. The method of claim 2 wherein heat generating compounds are selected from calcium chloride, magnesium chloride, aluminum chloride, ferric chloride, zinc chloride, magnesium sulfate, zinc sulfate, ferrous sulfate, aluminum sulfate, calcium sulfate, sodium sulfate, dry alum, calcium oxide, magnesium oxide, sodium carbonate, iron oxide, zinc oxide, zeolite, and sodium hydrogenphosphate and mixture thereof.

5. The method of claim 1 wherein the benefit component is a skin benefit agent, wherein said skin benefit agent is selected from a group consisting of anti-acne agents, emollients, non-steroidal anti-inflammatory agents, topical anaesthetics, artificial tanning agents, antiseptics, anti-microbial and anti-fungal actives, skin soothing agents, sunscreening agents, skin barrier repair agents, anti-wrinkle agents, anti-skin atrophy actives, lipids, skin lightening agents, sebum inhibitors, sebum inhibitors, skin sensates, protease inhibitors, skin tightening agents, anti-itch agents, hair growth inhibitors, desquamation enzyme enhancers, anti-glycation agents, and mixtures thereof.

6. The method of claim 5 wherein the skin benefit agent is selected from a group consisting of salicylic acid, niacinamide, ascorbic acid compounds, panthenol, tocopheryl nicotinate, flavonoids, farnesol, tocopherol, tocopherol esters, and mixtures thereof.

* * * * *